(12) United States Patent
Kambara et al.

(10) Patent No.: US 7,049,104 B2
(45) Date of Patent: May 23, 2006

(54) GENETIC ANALYSIS METHOD

(75) Inventors: Hideki Kambara, Hachioji (JP); Zheng Ping Li, Baoding (CN); Kazunori Okano, Shiki (JP); Keiichi Nagai, Higashiyamato (JP)

(73) Assignee: Hitachi, LTD, Tokyo (JP)

( * ) Notice: Subject to any disclaimer, the term of this patent is extended or adjusted under 35 U.S.C. 154(b) by 31 days.

(21) Appl. No.: 10/353,033

(22) Filed: Jan. 29, 2003

(65) Prior Publication Data

US 2003/0203381 A1 Oct. 30, 2003

(30) Foreign Application Priority Data

Apr. 24, 2002 (JP) ............................... 2002-121819

(51) Int. Cl.
*C12P 19/34* (2006.01)
*C12Q 1/68* (2006.01)

(52) U.S. Cl. .................... 435/91.2; 435/91.1; 435/6

(58) Field of Classification Search .................... 435/6, 435/91.1, 91.2; 536/24.3, 24.33, 23.1, 25.32, 536/22.1, 25.4
See application file for complete search history.

(56) References Cited

U.S. PATENT DOCUMENTS 5,595,890 A * 1/1997 Newton et al. ............ 435/91.2
6,841,055 B1 1/2005 Hayashizaki

FOREIGN PATENT DOCUMENTS

WO WO 01/62966 A2 * 8/2001
WO WO 02/18659 A2 8/2001

OTHER PUBLICATIONS

Pastinen et al. Multiplex, fluorescent, solid phase minisequencing for efficient screening of DNA sequence variation. Clinical Chemistry, vol. 42, No. 9, pp. 1301-1397, Sep. 1996.*

Bernat et al. Rapid identification of single nucleotide polymorphisms by fluorescence-based capillary electrophoresis. vol. 1, No. 1, pp. 72-78, Mar. 28, 2002.*

Brown et al. Fluorescent, Multiplexed, automated, primer-extension asay for 3120+1G to A and I148T mutations in Cystic Fibrosis. Clinical Chemistry, vol. 47, No. 11, pp. 2053-2055, Nov. 1, 2001.*

Tian et al. Rapid Detection of Deletion, Insertion, and substitution mutations via heteroduplex analysis using capillary- and microchip-based electrophoresis. Genome Research, vol. 10, pp. 1403-1413, 2000.*

Matyas et al. Quantificiation of single nucleotide polymorphisms: A novel method that combines primer extension assay and capillary electrophoresis. Human Mutation, vol. 19, pp. 58-68, Jan. 2002.*

Mostafa Ronaghi, Mathias Uhlen and Pal Nyren, "A Sequencing Method Based on Real-Time Pyrophosphate", Science. vol. 281 (Jul. 17, 1998), p. 363.

Hideki Kambara. Masao Kamahori. Kazunori Okano, Guohua Zou. "DNA". Jpn J. Elecroph. 2001:45: pp. 219-225, Abstract only.

"SNPs Analysis". Bio Wave. vol. 17 (2001). pp. 2-5, Abstract only.

* cited by examiner

*Primary Examiner*—Gary Benzion
*Assistant Examiner*—Cynthia Wilder
(74) *Attorney, Agent, or Firm*—Reed Smith LLP; Stanley P. Fisher, Esq.; Juan Carlos A. Marquez, Esq.

(57) ABSTRACT

The present invention relates to a quick and simple method for genetic testing, particularly for SNP testing, using two kinds of primers which are complementary to a mutant target and a wild-type target, respectively, and different in length or migration speed in electrophoresis. These probes are allowed to hybridize with targets, fluorophore-tagged nucleotides are attached to the primers, and electrophoresis is carried out for discriminatory detection.

9 Claims, 3 Drawing Sheets

GENETIC ANALYSIS METHOD

FIELD OF THE INVENTION

The present invention relates to methods for DNA detection, genetic testing, detection of DNA, such as detection of single nucleotide polymorphisms, genetic typing, and the like.

BACKGROUND OF THE INVENTION

The completion of the human genome sequence analysis is prompting a trend towards applying genetic information to diagnoses and the like in a medical field. A typical DNA analysis technique is gel electrophoresis and particularly capillary array gel electrophoresis apparatus is widely used as a high-speed, high throughput DNA analytical system and also for genome analysis. Following the genome sequence analysis, noticeable are gene expression profile analysis and analysis of single nucleotide polymorphisms (SNPs) in genes. Functions of genes and correlations between genes and diseases or drug sensitivity have been studied by examining genes expressed under various conditions or various gene mutations in individuals. Further, diagnosis of diseases and the like using such accumulated information on genes are about to be implemented.

In diagnoses of diseases, unlike in analysis of unknown gene, subjects to be tested are known genes or the presence or absence of mutations in such genes. The tests are desirably carried out at low cost and various test methods have been developed. Besides diagnosis of diseases based on a single gene, testing multiple genes has become important in relation to diseases caused by various genes and environmental effects and to drug sensitivity, in medical diagnosis. Accordingly, it is important to simultaneously examine various kinds of genes. Therefore, it is necessary to examine multiple genes instead of a single gene or mutation and thus there is a need for a system which includes processes for amplification of a region to be tested in a gene of interest and measures SNPs at low cost. For that purpose, a simple method which is different from capillary gel electrophoresis used in genome analysis is needed. Reported examples of the system to be used for SNP analysis or probe tests for genes include an invader assay, Taqman assay, DNA chip, and pyrosequencing (Science 281, 363 (1998)). The former three are detection methods using fluorophore tags, which include an excitatory laser light source and a light detection system. The pyrosequencing is a system using phased complementary strand extension and bio-luminescence, which includes a system for injecting a trace amount of nucleotide substrates in a designated order and a light detection system. Recently, the present inventors have reported a method for detecting SNPs, in which the 3'-terminal region of a primer is hybridized with a SNP site of a target DNA to proceed complementary strand extension and the resulting pyrophosphate is converted into ATP to generate bio-luminescence. In this case, the complementary strand extension characteristically takes place only when the primer is securely hybridized at the 3' terminus with the target DNA, thereby a wild-type target DNA and a mutant target DNA can be discriminated (Seibutsu Butsuri Kagaku 45, 219–225 (2001)). On the other hand, SNP analysis methods using gel electrophoresis have come into wide use. The simplest is a method in which a single-base complementary strand extension reaction is carried out using four kinds of fluorophore-tagged terminators and the fluorophore-tagged terminators and fluorophore-tagged DNAs are separated and measured using gel electrophoresis (Bio Wave 17, 2–5 (2001)). This method will be explained in detail since it mostly relates to the present invention. Multiple copies of a target DNA are prepared by PCR or the like. Although either double-stranded DNA or single-stranded DNA can be used for the analysis, a single-stranded DNA is used here as a target DNA to simplify the explanation. A primer, the 3' terminus of which is designed to come before the site to be tested for mutation of the target, is hybridized with the target to proceed single-base complementary strand extension. Here, four kinds of fluorophore-tagged terminators have been added in advance as a substrate for the complementary strand extension reaction. No further complementary strand extension takes place when any one of the nucleotide substrates (in this case, terminators) is incorporated. Only one of the fluorophore-tagged terminators is incorporated into the complementarily extended primer. Multiple fluorophores cannot bind to the primer to proceed complementary strand extension. The length of extended complementary strands thus formed is the same independently of the presence or absence of mutant bases in the target DNA and the kind of tagged fluorophores is different depending on the presence or absence of the mutation. Since a large number of unreacted fluorophore-tagged ddNTPs are present in the reaction solution, the fluorescence cannot be detected in this state. Accordingly, the fluorophore-tagged ddNTPs and extended fluorophore-tagged DNA strands are separated by gel electrophoresis and the kind of mutations (SNPs) is determined using a spectral fluorometer.

In a DNA testing method for medicinal diagnoses, for example, the following conditions are important: (1) costs for apparatus, reagents and the like are low, (2) high speed, high throughput detection is possible, (3) multiple DNA sites can be diagnosed simultaneously, and (4) a single-base mutation can distinguishably be detected. Among various methods, widely used is a method using a single-base complementary strand extension reaction, in which the reaction products are subjected to mass spectrometry or capillary gel electrophoresis analysis. However, a mass spectrometer is expensive and preparation of samples for the measurement is disadvantageously time consuming although the measurement itself can be done in a short time. On the other hand, in a method using capillary gel electrophoresis, the length of migration paths is long and it takes 30–60 minutes for detection since a commertially available DNA sequencer is used. Furthermore, four kinds of terminators (ddNTPs), each tagged with different fluorophores, are used as a substrate for complementary strand extension reaction and thus an expensive measuring instrument having a color differentiating function is required. The above mentioned methods are not necessarily suitable to carry out SNP measurement or high-throughput analysis readily in a short time and accordingly, the development of new technology for SNP analysis is in need.

SUMMARY OF THE INVENTION

In order to solve these problems, one kind of fluorophore is used and testing primers are designed to change the length of DNA strands, which are obtained by hybridizing the primers with target DNAs to proceed complementary strand extension, depending on whether the target DNAs have mutation or not. Further, in order to implement high-speed electrophoresis, capillary gel electrophoresis having short electrophoresis paths or gel electrophoresis paths made on a chip is introduced to obtain measurement results within 1–2 minutes.

First, a method which the present invention is based on will be explained. Probes (primers) for detection used herein are a mixture of a primer for mutant species, which is complementary to a mutant target, and a primer for wild-type species, which is complementary to a wild-type target. The primer for a wild-type species has a 10-mer poly T sequence (other sequences may be used) and migrates slower than the primer for a mutant species in electrophoresis. Thus they can be separately detected by electrophoresis. The probes (primers) are allowed to hybridize with target DNAs and DNA complementary strand extension is carried out by adding DNA polymerase, a reaction substrate dNTP (deoxynucleotide-3-phosphate) and a fluorophore-tagged terminator (ddNTP-f) (dNTP is not necessarily required). When a position complementary to a mutation site of the terminus of a primer is matched, the fluorophore-tagged ddNTP-f is incorporated and thus the primer is fluorophore-tagged. In contrast, when a position of a primer complementary to the mutation site of the target is not matched, no complementary strand extension takes place and thus the fluorophore tag is not incorporated. By making a base adjacent to or 2 bases apart from the terminal mutation site to be noncomplementary to a target, switching in the complementary strand extension reaction by match-mismatch can take place more accurately. A primer used for hybridization with a target has a length of about 20 mers. Two peaks with the same intensity appear with a hetero-type target containing wild type and mutant type. On the other hand, only one peak appears with a homo-type target containing either wild-type or mutant-type alone and accordingly, it is necessary to add a small amount of a fluorophore-tagged DNA strand as an internal standard to distinguish the peak. A peak due to a fluorophore-tagged nucleotide substrate (dNTP-f), which appears in a spectrum when a reaction product resulting from complementary strand extension is subject to electrophoresis as it is, can be used as an internal standard.

This specification includes part or all of the contents as disclosed in the specification and/or drawings of Japanese Patent Application No. 2002-121819, which is a priority document of the present invention.

EXPLANATIONS OF SYMBOLS

Figure 1A:
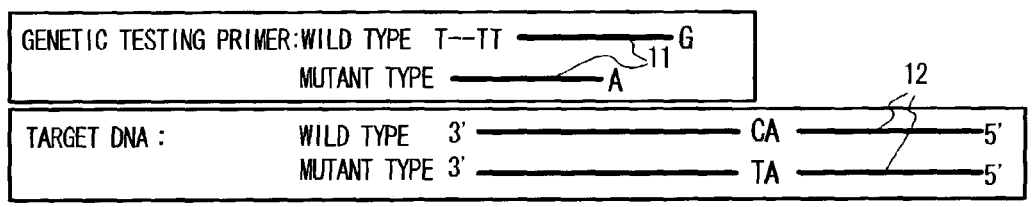
FIG. 1 illustrates the principle of the present invention.
Figure 1A:
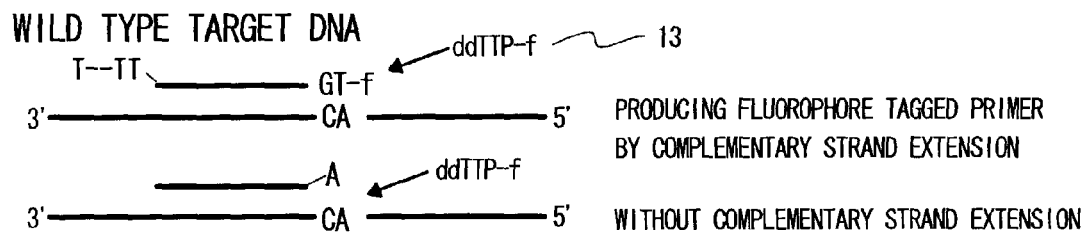
Figure 1B:
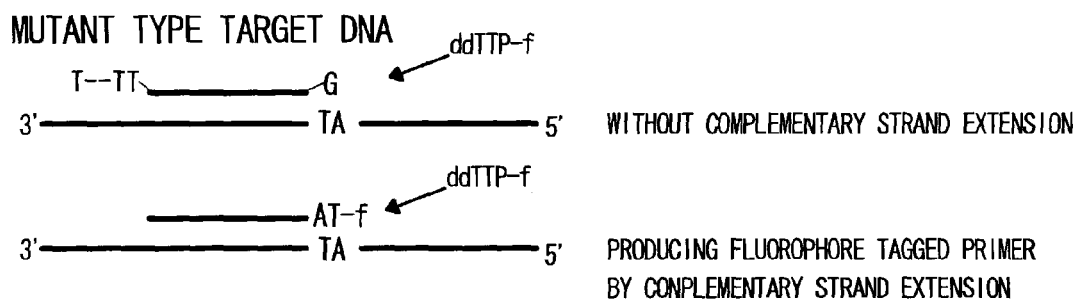
Figure 1B:
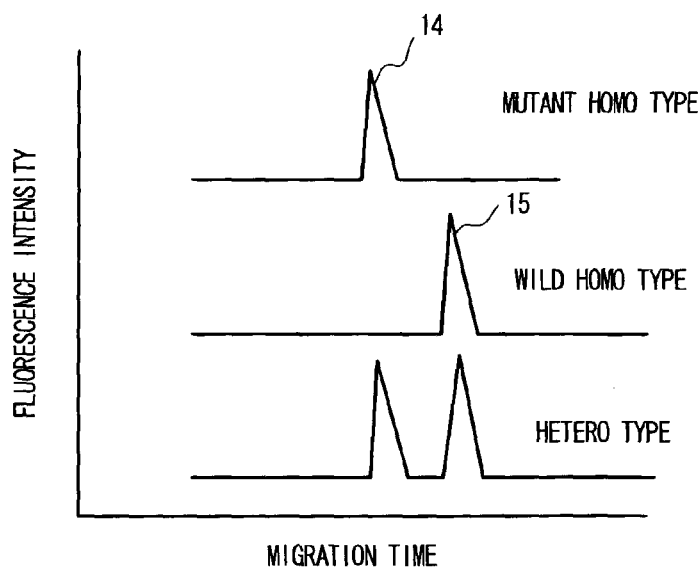

11: Region of genetic testing primer, which is complementary to the target

12: Sequence of the target to which the primer hybridizes

13: Fluorophore tag

14: Peak due to an oligomer without poly T, in which a fluorophore-tagged nucleotide is attached to the mutant primer for examining the mutant target.

15: Peak due to an oligomer with poly T, in which a fluorophore-tagged nucleotide is attached to the mutant primer for examining the wild-type target.

21: Fluorophore-tagged single-base extension product obtained with the mutant primer

22: Fluorophore-tagged single-base extension product obtained with the wild-type primer to which TTT is attached

23: Fluorophore-tagged single-base extension product obtained with the wild-type primer to which TTTTTT is attached

24: Fluorophore-tagged single-base extension product obtained with the wild-type primer to which TTTTTTTTT is attached

25: Fluorophore-tagged single-base extension product obtained with the wild-type primer to which T20 (20 linked Ts) is attached

41: Peak pattern obtained with one kind of mutant primer

42: Peak pattern obtained with a mixture of wild-type primers having different 2–3 mer poly T.

51: Pattern obtained from the hetero-type SNP testing site 1

52: Pattern obtained from the mutant SNP testing site 2

53: Pattern obtained from the wild-type SNP testing site 3

BEST MODE FOR CARRYING OUT THE INVENTION

The present invention will be hereinafter disclosed in detail.

EXAMPLE 1

The first example is an SNP typing, in which the 3' terminus of a testing primer is fit to a mutation site of a target DNA, a fluorophore-tagged terminator (dNTP-f) is incorporated into the primer by complementary strand extension and microchip electrophoresis or capillary electrophoresis is carried out using a fluidic polymer as a separation medium. In order to accomplish the SNP typing in a short time, it is necessary to use gel electrophoresis with a short migration path. A migration length of about 3–10 cm long is appropriate to analyse a fluorophore-tagged DNA of about 20 mers within 2–3 minutes. Microchip electrophoresis using grooves made on the surface of glass or plastic material as a migration path is used to obtain electrophoretic results in a short time using inexpensive apparatus which is commercially available from Hitachi Densi Engineering Inc. and Agilent Technologies. The apparatus is currently used mainly for checking the length of PCR products or the like. A DNA is fluorophore-tagged or stained with an intercalater dye inserted into a double-stranded DNA and is measured by laser excitation fluorometry. Inexpensive red laser is conveniently used and a DNA is tagged with a dye which is excitable by this laser, such as Cy-5, for the measurement. Simple apparatus can measure only one kind of fluorescence. It is difficult to distinguish DNAs having one-base length difference by microchip electrophoresis partly because of the short migration length. Therefore, if a sample for the measurement is prepared to make the difference in the length of strands as great as possible depending on whether a target is wild type or mutant, the SNP typing can be possible using gel electrophoresis with a short migration length. The present invention provides a method to realize this possibility.

A primer to match with a wild-type DNA and a primer to match with a mutant DNA are designed to be different in their length so as to be separated even by electrophoresis having a migration length as short as less than 10 cm. Namely, the primer for wild type has an additional oligonucleotide consisting of poly T at the 5' terminus so as to migrate slower than the mutant-type primer in electrophoresis. Therefore, these two primers are different only in the presence or absence of this poly T and whether the kind of nucleotide at the mutation site is complementary to a wild-type DNA or mutant type DNA (referred to as wild-type primer and mutant primer, respectively). FIG. 1 illustrates the principle of the present invention. Genetic testing primers containing a wild-type primer and a mutant primer in an equal concentration is prepared. The wild-type primer has a 10-mer poly T sequence at the 5' terminus. Sequences of primers used as an example are shown in SEQ ID NOs: 1 to 8 and sequences of target DNAs are shown in SEQ ID NOs: 9 to 12. A complementary strand extension reaction is carried out by adding a terminator (dNTP-f) complementary to the base species adjacent to the mutation site of interest of the target DNA, in this case dTTP-f, and DNA polymerase. When the 3' terminus of the primer is complementary to the target, complementary strand extension takes place starting from the primer. When the 3' terminus is noncomplementary, the complementary strand extension does not take place and thus no fluorophore tag is incorporated. In this case, the extension is with a single base; however, a multiple base extension reaction can take place by adding dNTPs (other than the base of the terminator) and a fluorophore-tagged terminator to incorporate the fluorophore-tagged terminator. In any case, the base length of the extension is the same with wild type and mutant type but whether the complementary strand extension takes place, or whether the fluorophore tag is incorporated or not, is determined depending on which type the target is. Examples of DNA polymerase to be used include Thermo Sequenase DNA Polymerase (Amersham Biosciences), Sequenase Ver. 2 T7 DNA Polymerase (Amersham Biosciences), and Exo-Klenow (Ambion). In all these enzymes, 5'→3' exonuclease activity and 3'→5' exonuclease activity are lost by genetic engineering. In particular, it is important that the enzyme to be used in the present invention is free of exonuclease activity (3'→5' exonuclease activity) which cleaves the 3' terminus of the primer. This is because if the 3' termini of primers are cleaved by the exonuclease, complementary strand extension takes place in both wild-type primer and mutant primer independently of the structure of the 3' terminus in case where the 3' terminus of the primer and the target DNA are mismatched. In the example of the present invention, heat-resistant enzyme Thermo Sequenase DNA Polymerase is used to reduce the effect of higher order structure of primers, which interferes with complementary strand extension, and to make it possible to measure a wild type and mutant type even in a double-stranded DNA. A fluorophore tag used is Cy-5 and ddNTP-Cy5 used is a product of Amersham Bioscience, Thermo Sequenase Cy5 Dye Terminator Kit (stocks are ddATP-Cy5: 8.8 μM, ddCTP-Cy5: 7.0 μM, ddGTP-Cy5: 17.6 μM, and ddTTP-Cy5: 14.3 μM).

A target DNA is prepared by an ordinary method in which DNA is extracted from the blood and a site of interest is amplified by PCR. Namely, the red blood cells are destroyed by adding 18 ml of 50 mM NaCl solution to 2 ml of whole blood. Precipitate is obtained by centrifugation at 3500 rpm for 15 minutes at 4° C. The resulting precipitate is washed with a 50 mM NaCl solution to obtain a leukocyte fraction. One ml of DNAzol (Gibco BRL) is added to dissolve cell walls. The genomic DNA is cut short by putting in and out the solution using a syringe with an 18G needle. Insolubles are removed by centrifugation. After adding 0.5 ml of ethanol and stirring, the genomic DNA is recovered by centrifugation. After rinsing with 70% ethanol, 400 μl of water is added and the DNA is dissolved at 65° C. RNA is decomposed by adding 8 μl of 100 mg/ml RNase A and incubating at 37° C. for 2 hours. The enzyme is inactivated by adding 400 μl of a mixture of phenol, chloroform, and amyl alcohol. The genomic DNA is recovered by propanol precipitation and then dissolved in 200 μl of 0.5×TE (pH 8.0). An about 100 μg/ml genomic DNA solution is obtained by this procedure. In order to obtain a single-stranded DNA, biotin is attached to one side of a PCR primer and PCR products are captured by magnetic beads, on the surface of which avidin is immobilized, and a single-stranded DNA is obtained by heat inactivation or the like and used as a target DNA. Namely, to 1 μl of the genomic DNA sample prepared as described above are added 5 μl of 10×PCR buffer solution attached to Hot Star Taq (Quagen), 2 μl of 5 mM dNTP, 5 μl each of 2 kinds of primers for PCR (1 pmol/μl), 37 μl of water and 0.25 μl of Hot Star Taq and then the admixture is heated at 95° C. for 10 minutes, after which steps at 94° C. for 30 seconds, at 57° C. for 30 seconds and at 72° C. for 60 seconds are repeated 30 times to amplify a specific DNA region. Free primers remaining in the PCR products are removed using a QIAquick PCR purification kit (Quagen) because they decrease the yield of single-stranded DNA preparation using beads in a later stage.

To the PCR products are added 1 μl of magnetic beads Dynabeads (M280) Streptavidin (Dynal, 6.7×10$^8$ beads/ml) and 25 μl of a solution (2 M NaCl, 1 mM EDTA, 0.02% NP-40, 10 mM Tris-HCl, pH 7.5) and then the admixture is stirred at 25° C. for 30 minutes. The magnetic beads onto which the PCR products are captured are recovered by a magnet, suspended in 100 μl of 0.1 M NaOH and allowed to stand for 5 minutes, after which the beads are washed and a single-stranded DNA immobilized on the beads or a single-stranded DNA suspended in the NaOH solution is obtained. The single-stranded DNA immobilized on the beads is suspended in 10 μl of water and used as a sample. The single-stranded DNA suspended in the NaOH solution is immediately neutralized with 3 M acetic acid, precipitated with ethanol, dissolved in 10 μl water and used as a sample. Primers (10 pmol each) are added each of the samples and an extension reaction is carried out using a Thermo Sequenase system, after which Cy5 ddNTP incorporated is measured by electrophoresis. More specifically, for a reaction volume of 10 μl, 10 pmol each of primers for wild type and mutant type, 20–40 pmol ddNTP-Cy5 corresponding to the target DNA, 1 μl of 10× buffer solution attached to the enzyme and 2 units of Thermo Sequenase are added to the abovementioned single-stranded DNA (most preferably 0.4–1 pmol) on ice, and then the admixture is immediately subjected to 30 cycles of steps at 94° C. for 30 seconds, at 54° C. for 30 seconds and at 72° C. for 30 seconds, after which an extension reaction is carried out at 72° C. for 2 minutes. After the extension reaction, 5 μl of formamide containing 1 mM EDTA (pH 8) is added to 5 μl of the resulting solution and the admixture is subjected to heat denaturation at 80° C. for 3 minutes and then cooled on ice. The whole volume is subjected to the following separation analysis by electrophoresis.

Figure 2:
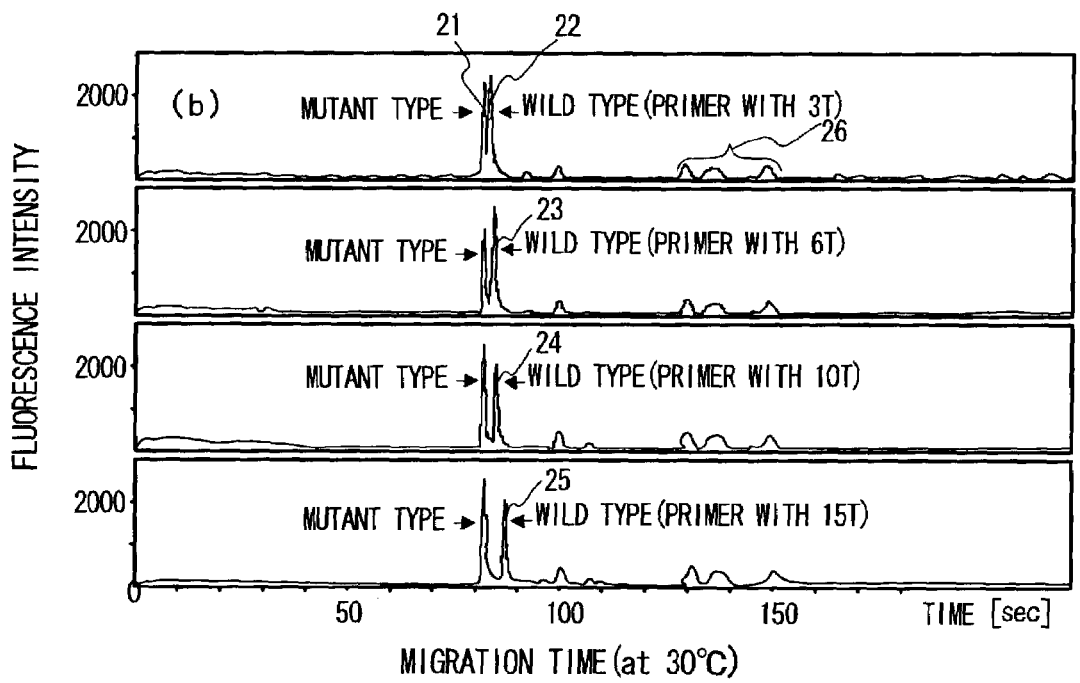
FIG. 2 illustrates separability using various poly T tails.

Electrophoretic separation is carried out using electrophoresis apparatus "Cosmo-i" made by Hitachi Densi Engineering Inc. coupled with an electrophoresis part "I-chip" made by Hitachi Kasei. This is an electrophoresis chip using a fluidic polymer as a separation medium. The migration length is about 4 cm; and separation analysis is difficult with strands having a several base length difference but is possible with strands having a more than 10 base length difference. FIG. 2 shows electrophoresis spectra of DNA strands, in which the length of poly T tail of SEQ ID NO: 1 is changed and a fluorophore-tagged terminator is introduced at the 3' terminus by complementary strand extension. 21 is a mutant primer represented by SEQ ID NO; 2 and has 21 mers, 22 is a wild-type primer represented by SEQ ID NO: 1 and has a poly-T length of 2, 23 is a wild-type primer represented by SEQ ID NO: 1 and has a poly-T length of 5, and 24 is a wild-type primer of SEQ ID NO: 1 and have a poly-T length of 9. It is shown that the mutant primer and wild-type primer can be well distinguished when the difference in poly-T length is 5 or more. The time required for gel electrophoresis is 1–2 minutes. The poly-T length of more than 20 mers is not desirable because the migration time increases and the signal may overlap with that of ddNTP. Peaks of the fluorophore-tagged primers appear in an area without background fluorescence, which results in a highly accurate measurement.

Typing was carried out with various SNPs other than those above. As a result, it was confirmed that the typing could be completed within 1–2 minutes with a sufficient accuracy. In electrophoresis, running time may change depending on conditions. Therefore when a single peak is observed, it is difficult to determine whether it is mutant type or wild type. However, in this case, remaining fluorophore-tagged ddNTP-f appears and is conveniently used as a standard for determination. Further, since ddNTP-f comes after the signal from the primers, the complementary strand extension sample can be conveniently used as a sample for measurement without further purification.

It is confirmed that the SNP detection of the present invention can be carried out using the genomic DNA thus prepared. The following example is to explain details directly related to the present invention using chemically-synthesized DNA sequences represented by SEQ ID NOs: 9 to 12 as a model template.

Wild-type and mutant primers and fluorophore-tagged terminators corresponding to samples 2, 3 and 4 are as follows.

Sample 2:
Wild-type primer 3'-CtTccatgatataaccattcttttttttttt-5' (SEQ ID NO: 3)
Mutant primer 3'-GtTccatgatataaccattct-5' (SEQ ID NO: 4)
Terminator ddTTP-f Sample 3:
Wild-type primer 3'-AcGtagtgctccaatcctcaattttttttttt-5' (SEQ ID NO: 5)
Mutant primer 3'-GcGtagtgctccaatcctcaa-5' (SEQ ID NO: 6)
Terminator ddCTP-f Sample 4:
Wild-type primer 3'-CaGcagctccttaagattacgttttttttttt-5' (SEQ ID NO: 7)
Mutant primer 3'-AaGcagctccttaagattacg-5' (SEQ ID NO: 8)
Terminator ddTTP-f One kind of terminator alone is used in this case; however, all SNPs can be detected if a reagent kit containing remaining 3 kinds of nucleotide substrates (dNTPs) in addition to the terminator is provided. In such a case, although the length of complementary strand extension changes depending on the target and the complementary strand extension may stop when the terminator is incorporated after the extension with several bases, the difference in the strand length between the mutant type and wild type is again 10 bases.

EXAMPLE 2

The second example uses primers in which the 3' terminus comes several bases ahead of a mutation site. The structure

```
Sample 1:
5'-CCGAG GCATAGTAGA C/T GACTGGATAT AGGGACCTAC-3'   (SEQ ID NO: 9)

Sample 2:
5'-AAAAT ATAAAATAAA G/C ATGGTACTAT ATTGGTAAGA-3'   (SEQ ID NO: 10)

Sample 3:
5'-GGAGG CTGAGGTGGG T/C GGATCACGAG GTTAGGAGTT-3'   (SEQ ID NO: 11)

Sample 4:
5'-TTGGT CCCTGTCCTA G/T TGGTCGAGGA ATTCTAATGC-3'   (SEQ ID NO: 12)
```

For Sample 1, 3'-GcAgacctatatccctggatgttttttttt-5' (SEQ ID NO: 1) is used as a wild-type primer. On the other hand, 3'-AcAgacctatatccctggatg-5 (SEQ ID NO: 2) is used as a mutant primer. Genetic testing primers are a 1:1 mixture of the two primers and are hybridized with the 3'-terminal side of a mutation site of the target sample. The 3' terminus of the primers is designed to come to the mutation site. The base species at the third position from the 3' terminus of the primers is selected to mismatch with the target. This allows the 3' terminus of the primers to readily come off due to mismatch of the base species at the mutation site and thus complementary strand extension can be completely blocked. Furthermore, the complementary strand extension partially takes place when a mismatch is present only at the 3' terminus and such an artificial mismatch is not introduced into the primer, which may results in less accurate typing. A fluorophore-tagged terminator to be added is ddTTP-f.

of the terminal regions of the primers will be explained using Sample 1 as an example. The primers are prepared so that the third base from the terminus corresponds to the mutation site of the target. Primers for Sample 1 are as follows:

Wild-type primer: 3'-ctGGtgacctatatccctggttttttttttt-5' (SEQ ID NO: 13)
Mutant primer: 3'-ctAGtgacctatatccctgg-5' (SEQ ID NO: 14)

The base at the third position from the 3' terminus recognizes the target and determines whether to proceed complementary strand extension or not. In this example, a mismatched base G (originally C) is placed at the fourth position so that the 3' terminus comes off and no complementary strand extension takes place when the third base is mismatched. This artificial mismatch can be placed at the second base position. Various modifications, are possible since the only requirement is in control complementary strand extension capability by changing stability of hybridization at the terminus depending on whether the base of the primer and the base of the target at the mutation site of interest are complementary or not. When ddTTP-f is introduced as a substrate for complementary strand extension, the reaction stops after single base extension and accordingly, the resulting product is 3'-T(-f)ctGGtgacctatatccctggttttttttt-5' (SEQ ID NO: 17) in the case of wild type or 3'-T(-f) ctAGtgacctatatccctgg-5' (SEQ ID NO: 18) in the case of mutant type. Here, "(-f)" indicates that a fluorophore is attached to the nucleotide base T. As a substrate for complementary strand extension reaction, a mixture of dNTP and ddNTP, for example, ddCTP-f and dTTP can be used. In this case, one each of dTTP and ddCTP is incorporated and 2-base extension takes place. The resulting fluorophore-tagged fragment is 3'-C(-f)tctGGtgacctatatccctggttttttttt-5' (SEQ ID NO: 19) in the case of wild type or 3'-C(-f) tctAGtgacctatatccctgg-5' (SEQ ID NO: 20) in the case of mutant type. Both of them migrate faster than ddCTP-f in electrophoresis and results can be obtained within 2 minutes. A condition that ddNTP-f migrates slower than the fluorophore-tagged fragment can be made by using Cy5, Cy5.5 or Texas Red as a fluorophore. This condition is strongly due to the charge of fluorophores and accordingly, cannot be established with fluorophores having a negative charge, such as fluorescein, since such ddNTP-f migrates fast.

EXAMPLE 3

The third example is allele frequency analysis. In the case of SNP analysis for individuals, 3 kinds of spectral patterns appear, i.e., wild homo type, mutant homo type and hetero type. Here, detailed quantitative analysis, for example, to find out the percentage of mutant type is not necessary. SNP typing means to determine which one of the three types the target belongs to. In order to investigate the relationship between SNPs and drug sensitivity or sensitivity related to diseases, SNPs in an extremely large population, i.e., as many as tens of thousands of patients, have to be examined to elucidate the correlation with these sensitivities. Since the number of SNPs is said to be several millions, it will take a great deal of labor to examine SNPs one by one. Therefore, a screening method is suggested to be appropriate, in which samples from patients are sorted and pooled for SNP measurement according to symptoms of the diseases or the type of drug response to investigate correlation between SNPs and the diseases or drug response. For this, it is necessary to isolate and accurately detect products which are simultaneously obtained under the same conditions by complementary strand extension using a mutant target and wild-type target as a template. In an SNP typing method using complementary strand extension and gel electrophoresis, in which single-base extension takes place by complementary strand extension using four kinds of fluorophore-tagged ddNTPs, the complementary strands obtained from the mutant type and the complementary strand obtained from the wild-type have the same base length and accordingly peaks separated by electrophoresis overlaps. Their relative ratios can be calculated by color separation detection; however, the drawback is a big error. In the present invention, complementary strand extension takes place with the same dye under the same conditions and the resulting strands are separated by electrophoresis and detected by the same detector, which is more suitable for quantitative evaluation. This method is appropriate for quantitative study since DNAs having a more than 10 base length difference can completely be distinguished as separate peaks even by microchip electrophoresis which completes electrophoresis in a short time.

Figure 3:
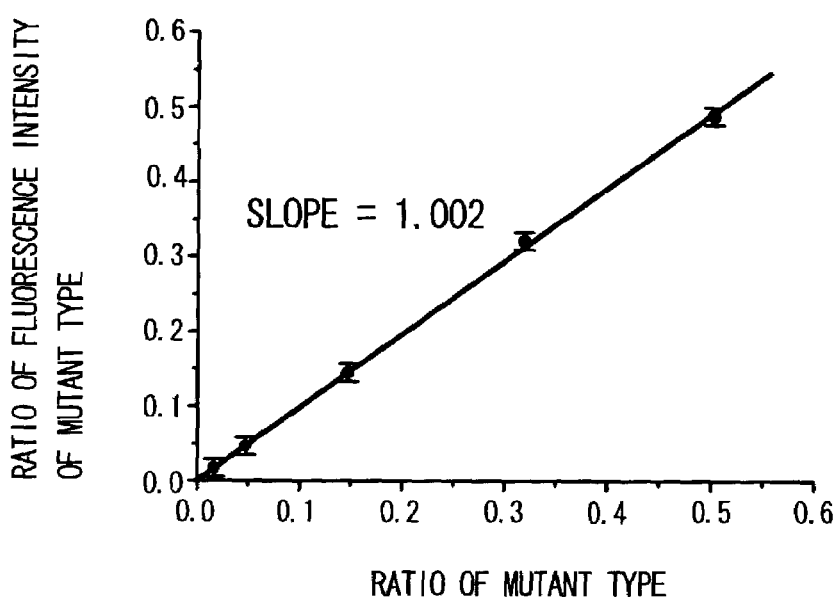
FIG. 3 shows a calibration curve for quantitative SNP analysis.

FIG. 3 shows a calibration curve 31, in which a relative intensity of mutant DNA (Im) is expressed by making the sum of signal intensity of the mutant primer (Im) and signal intensity of the wild-type primer (Iw), i.e., (Im+Iw), a denominator. The point 32 is a plot for 1% mutant DNA. This result shows that the analysis is possible at an accuracy of less than 1%. This method is proved to be effective to examine an abundance of mutant species since the amount of mutant species present is proportional to the signal intensity. Although such analysis is particularly important as a pooled sample analysis, no appropriate method has been available and a new method has been expected. It is also effective to introduce a mutant primer in a large amount relative to a wild-type primer for measurement to analyze low abundance allele frequencies. In this way, a large amount of complementary strand extension products, in which fluorophore tags are incorporated into the mutant type, are produced and thus the mutant type present at a low frequency can be more easily measured.

EXAMPLE 4

This is an example of simultaneous typing of multiple samples. In this case, it is necessary to identify peaks by separately detecting signals corresponding to multiple sites of mutation. The horizontal axis of an electrophoresis spectrum, namely migration time, changes depending on conditions. Therefore, peaks have to be identified, for example, by conducting every electrophoresis run with a standard substance. Disclosed is a method appropriate to identify whether a readily observed signal is due to a mutant target or a wild-type target.

Figure 4:
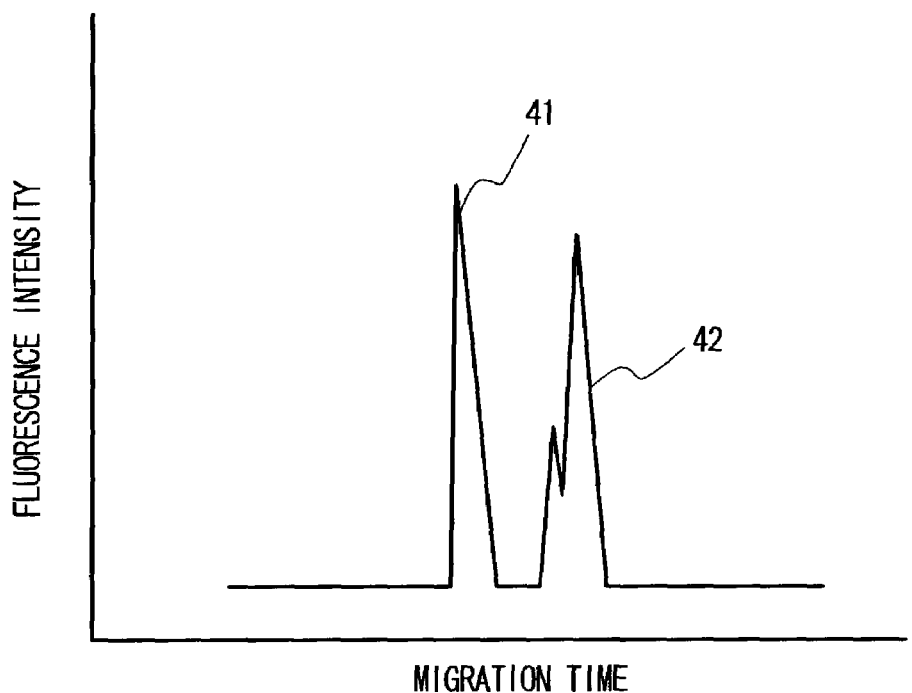
FIG. 4 shows results of the discrimination of peaks using spectral patterns.
Figure 5:
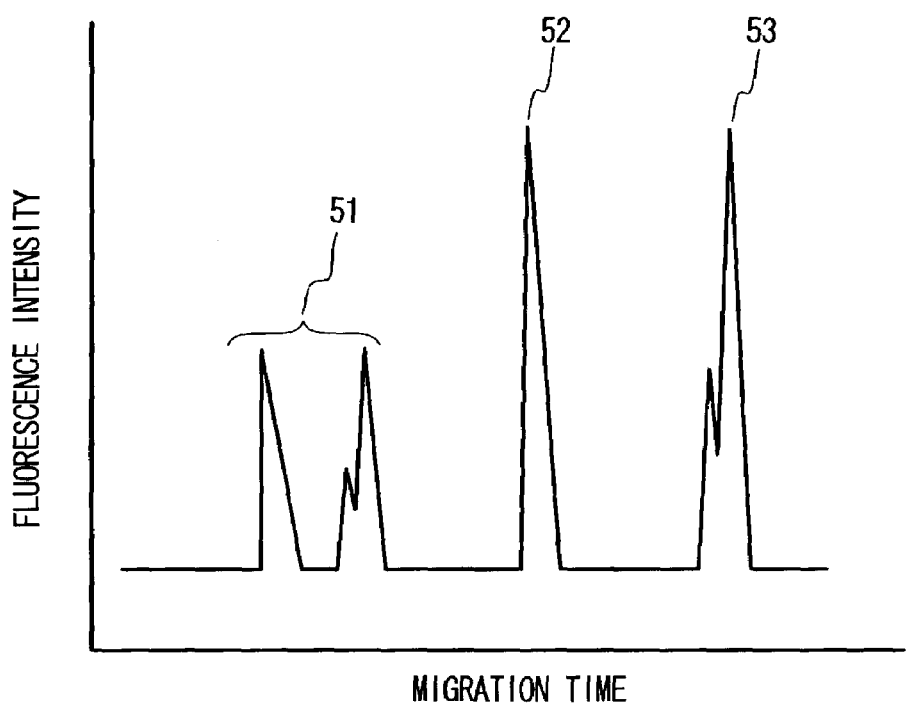
FIG. 5 is a schematic representation of mixed analysis.

A pattern appears on a electrophoresis spectrum is generally one peak. Peaks can be separately detected by changing the shape of the peaks without the need for a standard substance or by narrowing the distance between a peak due to a wild type and a peak due to a mutant type. In this example, two wild-type primers having attached poly T of different length (any primers having different migration time) are used to form characteristic peaks on a spectrum. More specifically, the wild-type primers for Sample 1 are 3'-ctGGtgacctatatccctggttttt-5' (SEQ ID NO: 15) and 3'-ctGGtgacctatatccctggttt-5' (SEQ ID NO: 16) and the ratio is 2:1, i.e., 5 pmol to 2.5 pmol (50 µl in volume). On the other hand, a mutant primer is 3'-ctAGtgacctatatccctgg-5' (5 pmol) (SEQ ID NO: 14). The lengths of the poly T attached to the wild-type primers are 3 bases and 6 bases, which are shorter than those used in the previous example. As shown in FIG. 4, the mutant type and the wild type can be readily discriminated from the shape of the spectrum pattern obtained. In the case where multiple SNPs are to be examined, first a region of interest is amplified from the genome as described above, for example, by PCR, to obtain multiple DNA fragments, after which a target DNA strand is obtained as a single strand as described above. The testing primers corresponding to each of the SNPs are mixed with the sample and hybridization is carried out. Complementary strands are synthesized by adding four kinds of dNTP-f tagged with Cy-5 (any different fluorophore can be used). Of course, a combination of ddNTP-f and dNTP or dNTP-f and ddNTP can be used. The lengths of the testing primers and the migration time are adjusted so that the fluorophore-tagged complementary strand extension reaction products appear at different positions depending on the kind of SNPs. FIG. 5 shows an example of the measurement for multiple (3 different) samples. Three sets of the primers are prepared as probe set each of which has different length of the sequence. The difference is 10 bases. Each probe set has wild type probe and the probe further having three poly-T bases. The peak group of 51, 52, and 53 shows the peaks derived from three samples, respectively. Concerning about peak 51, the left peak shows the wild type and the right peak shows the mutant type. 52 and 53 show substantially one peak, respectively. The peak of the mutant type is detected shown as peak 52. The peak of the wild type is detected shown as peak 53. Either a wild-type or a mutant-type peak is always observed for all SNPs. Occasionally, both signals are observed. A closer observation on the shape of the peaks finds three adjacent peaks, i.e., a low peak in the center and flanking high peaks, in the case of hetero type. Since either one of the high peaks disappears in the case of homo type (the low peak also disappears in the case of mutant type), the type of the SNPs can be readily discriminated. Thus, all the SNPs can be identified.

EXAMPLE 5

Although effectiveness has been described above mainly focusing on SNP typing, the method can also be applicable to ordinary genetic typing (to examine the presence or absence of a sequence of interest in DNA samples to be tested). Probes having various lengths are prepared to be hybridized to a site of testing. In order to discriminate peaks appeared on electrophoresis patterns, some probes (primers) are designed to have the same sequence at the hybridization site but have additional 1–2 bases such as T and A attached to their 5' termini, and are mixed at a certain ratio. The peaks can be easily identified from the shape since the shape of the peaks which appear in the resulting spectrum pattern reflects this mixing ratio, even if various peaks appear in parallel or change in migration speed interferes the simple peak identification by migration time. Electrophoresis of multiple DNA probes in a single run sometimes causes problems such as poor isolation capability; however, in this case, sorted samples can be separated by electrophoresis at uniformly spaced intervals and serially analyzed. A particular advantage is that not much time is required for repetitive measurements since electrophoresis can be completed in a short time.

INDUSTRIAL APPLICABILITY

The present invention provides a simple, high-throughput analysis method using inexpensive apparatus, in which two primers (probes) with different lengths is prepared for one target DNA sequence site and allowed to hybridize with a target simultaneously, the resulting hybridized strands where capable of proceeding complementary strand extension, form complementary strand extension with the same number of bases and at the same time incorporate fluorophore tags, after which discriminatory detection can be carried out in a short time using short and quick electrophoresis. In the case of SNP analysis, two primers, i.e., one wild-type primer to match with a wild-type target DNA and one mutant primer to match with a mutant target DNA are used for testing and a fluorophore-tagged nucleotide is introduced at the terminus of a primer upon complementary strand extension. Here, the fluorophore-tagged nucleotide is introduced only into the primer that matches with a target. The mutant primer and the wild-type primer are designed to be different in length and separately detectable in a short time using short electrophoresis. The complementary strand extension takes place only with primers matched with a target and the number of bases to be extended is the same in the wild type and mutant type. Therefore, if the two primers are different in length, they can be easily discriminated. Here, poly T is attached to the 5' terminus of the wild-type primer; however, radicals other than DNA may also be attached to change the migration speed in electrophoresis. In any case, the electrophoresis for separation has to be performed in a short time. Consequently, the presence or absence of mutation can be examined within 1–2 minute. Roughly 2000 mutations can be measured in one hour using an instrument having 100 migration paths, assuming that one measuring cycle takes 3 minutes at the longest. Further, high-throughput SNP typing, as many as 20,000 SNP typings a day, is possible by operating 10 hours per day. Furthermore, the method is applicable to measure an abundance of mutant DNA, which is important in studying correlation between SNPs and drug sensitivity and thus greatly contributes to the field of DNA detection.

All publications, patents and patent applications cited herein are incorporated herein by reference in their entirety.

The invention claimed is:

1. A genetic analysis method, comprising the steps of:
performing a complementary strand extension reaction on a testing site of a DNA sequence using a mixture of first primers, matching with mutant type, and second primers, matching with wild type as genetic testing probes, so as to incorporate a fluorophore tag during said extension reaction thereby obtaining fluorophore-tagged DNA strands; and
separating the fluorophore-tagged DNA strands by electrophoresis,
wherein at least a nucleotide at the testing site is different between the first primers and the second primers, the first primers or the second primers having additional other sequence to shift migration speed in electrophoresis, both of the first primers and the second primers having same base sequence except the nucleotide at the testing site and the additional other sequence, and fluorophore tags in the fluorophore-tagged DNA strands are of same dye.

2. A genetic analysis method according to claim 1, wherein bases at said testing site are different between the first primers and the second primers and a length of extended strands of the first primers and the second primers are different.

3. A genetic analysis method according to claim 1, wherein a fluorophore-tagged deoxynucleotide tri-phosphate (dNTP) or di-deoxynucleotide tri-phosphate (ddNTP) is incorporated during the complementary strand extension reaction and products of the complementary strand extension are detected by fluorophore detection.

4. A genetic analysis method according to claim 1, wherein the electrophoresis is microchip electrophoresis in which migration paths are formed by cutting grooves or setting capillaries and a length of each of the migration paths is less than 10 cm.

5. A genetic analysis method according to claim 1, wherein a 3' terminus or a 3' terminal region of the first primers and the second primers are designed to hybridize with a site of mutation to be examined in matching with a target, a ddNTP-fluorophore or a fluorophore-tagged dNTP being incorporated during the complementary strand extension reaction.

6. A genetic analysis method according to claim 1, wherein a DNA strand incorporated with a fluorophore-tagged nucleotide substrate by the complementary strand extension reaction migrates faster than the fluorophore-tagged nucleotide substrate during the electrophoresis.

7. A genetic analysis method according to claim 1, wherein a nucleotide analogue homologous to deoxynucleotide tri-phosphate(dNTP) or di-deoxynucleotide tri-phosphate (ddNTP) is used as a substrate for said complementary strand extension reaction.

8. A genetic analysis method by electrophoresis comprising steps of:
performing a single-base or multiple-base complementary strand extension reaction using a gel or fluidic polymer, and a set of primers; and
observing shapes of peaks of electrophoresis patterns of DNA bands seen in electrophoretic separation after incorporation of a fluorophore tag, wherein the primers have same base sequence except at least a nucleotide at a testing site and an additional other sequence, fluorophore tags in the fluorophore-tagged DNA strands are of same dye and the shapes of peaks are different depending on the types of a respective target sites.

9. A genetic analysis method according to claim 8, wherein length of extended strands of the first primers and the second primers are different.

* * * * *

SEQUENCE LISTING

<160> NUMBER OF SEQ ID NOS: 16

<210> SEQ ID NO 1
<211> LENGTH: 31
<212> TYPE: DNA
<213> ORGANISM: Artificial Sequence
<220> FEATURE:
<223> OTHER INFORMATION: DNA primer which hybridize with a DNA template
      represented by SEQ ID NO: 9 and be complementary extend to the DNA
      template represented by SEQ ID NO: 9

<400> SEQUENCE: 1
cttccatgat ataaccattc tttttttttt t                                    31

<210> SEQ ID NO 2
<211> LENGTH: 21
<212> TYPE: DNA
<213> ORGANISM: Artificial Sequence

```
<220> FEATURE:
<223> OTHER INFORMATION: DNA primer which hybridize with a DNA template
      represented by SEQ ID NO: 9 and be complementary extend to the DNA
      template represented by SEQ ID NO: 9

<400> SEQUENCE: 2
acagacctat atccctggat g                                             21

<210> SEQ ID NO 3
<211> LENGTH: 31
<212> TYPE: DNA
<213> ORGANISM: Artificial Sequence
<220> FEATURE:
<223> OTHER INFORMATION: DNA primer which hybridize with a DNA template
      represented by SEQ ID NO: 10 and be complementary extend to the
      DNA template represented by SEQ ID NO: 10

<400> SEQUENCE: 3
cttccatgat ataaccattc tttttttttt t                                  31

<210> SEQ ID NO 4
<211> LENGTH: 21
<212> TYPE: DNA
<213> ORGANISM: Artificial Sequence
<220> FEATURE:
<223> OTHER INFORMATION: DNA primer which hybridize with a DNA template
      represented by SEQ ID NO: 10 and be complementary extend to the
      DNA template represented by SEQ ID NO: 9

<400> SEQUENCE: 4
gttccatgat ataaccattc t                                             21

<210> SEQ ID NO 5
<211> LENGTH: 31
<212> TYPE: DNA
<213> ORGANISM: Artificial Sequence
<220> FEATURE:
<223> OTHER INFORMATION: DNA primer which hybridize with a DNA template
      represented by SEQ ID NO: 11 and be complementary extend to the
      DNA template represented by SEQ ID NO: 11

<400> SEQUENCE: 5
acgtagtgct ccaatcctca attttttttt t                                  31

<210> SEQ ID NO 6
<211> LENGTH: 21
<212> TYPE: DNA
<213> ORGANISM: Artificial Sequence
<220> FEATURE:
<223> OTHER INFORMATION: DNA primer which hybridize with a DNA template
      represented by SEQ ID NO: 11 and be complementary extend to the
      DNA template represented by SEQ ID NO: 11

<400> SEQUENCE: 6
gcgtagtgct ccaatcctca a                                             21

<210> SEQ ID NO 7
<211> LENGTH: 31
<212> TYPE: DNA
<213> ORGANISM: Artificial Sequence
<220> FEATURE:
<223> OTHER INFORMATION: DNA primer which hybridize with a DNA template
      represented by SEQ ID NO: 12 and be complementary extend to the
      DNA template represented by SEQ ID NO: 12

<400> SEQUENCE: 7
cagcagctcc ttaagattac gttttttttt t                                  31
```

```
<210> SEQ ID NO 8
<211> LENGTH: 21
<212> TYPE: DNA
<213> ORGANISM: Artificial Sequence
<220> FEATURE:
<223> OTHER INFORMATION: DNA primer which hybridize with a DNA template
      represented by SEQ ID NO: 12 and be complementary extend to the
      DNA template represented by SEQ ID NO: 12

<400> SEQUENCE: 8
aagcagctcc ttaagattac g                                         21

<210> SEQ ID NO 9
<211> LENGTH: 36
<212> TYPE: DNA
<213> ORGANISM: Artificial Sequence
<220> FEATURE:
<223> OTHER INFORMATION: DNA template

<400> SEQUENCE: 9
ccgaggcata gtagaygact ggatataggg acctac                         36

<210> SEQ ID NO 10
<211> LENGTH: 36
<212> TYPE: DNA
<213> ORGANISM: Artificial Sequence
<220> FEATURE:
<223> OTHER INFORMATION: DNA template

<400> SEQUENCE: 10
aaaatataaa ataaasatgg tactatattg gtaaga                         36

<210> SEQ ID NO 11
<211> LENGTH: 36
<212> TYPE: DNA
<213> ORGANISM: Artificial Sequence
<220> FEATURE:
<223> OTHER INFORMATION: DNA template

<400> SEQUENCE: 11
ggaggctgag gtgggyggat cacgaggtta ggagtt                         36

<210> SEQ ID NO 12
<211> LENGTH: 36
<212> TYPE: DNA
<213> ORGANISM: Artificial Sequence
<220> FEATURE:
<223> OTHER INFORMATION: DNA template

<400> SEQUENCE: 12
ttggtccctg tcctaktggt cgaggaattc taatgc                         36

<210> SEQ ID NO 13
<211> LENGTH: 30
<212> TYPE: DNA
<213> ORGANISM: Artificial Sequence
<220> FEATURE:
<223> OTHER INFORMATION: DNA primer which hybridize with a DNA template
      represented by SEQ ID NO: 9 and be complementary extend to the
      DNA template represented by SEQ ID NO: 9

<400> SEQUENCE: 13
ctggtgacct atatccctgg tttttttttt                                30

<210> SEQ ID NO 14
<211> LENGTH: 20
```

```
-continued

<212> TYPE: DNA
<213> ORGANISM: Artificial Sequence
<220> FEATURE:
<223> OTHER INFORMATION: DNA primer which hybridize with a DNA template
      represented by SEQ ID NO: 9 and be complementary extend to the
      DNA template represented by SEQ ID NO: 9

<400> SEQUENCE: 14
ctagtgacct atatccctgg                                                 20

<210> SEQ ID NO 15
<211> LENGTH: 26
<212> TYPE: DNA
<213> ORGANISM: Artificial Sequence
<220> FEATURE:
<223> OTHER INFORMATION: DNA primer which hybridize with a DNA template
      represented by SEQ ID NO: 9 and be complementary extend to the
      DNA template represented by SEQ ID NO: 9

<400> SEQUENCE: 15
ctggtgacct atatccctgg tttttt                                          26

<210> SEQ ID NO 16
<211> LENGTH: 23
<212> TYPE: DNA
<213> ORGANISM: Artificial Sequence
<220> FEATURE:
<223> OTHER INFORMATION: DNA primer which hybridize with a DNA template
      represented by SEQ ID NO: 9 and be complementary extend to the
      DNA template represented by SEQ ID NO: 9

<400> SEQUENCE: 16
ctggtgacct atatccctgg ttt                                             23
```